United States Patent [19]
Nields

[11] Patent Number: 5,776,062
[45] Date of Patent: Jul. 7, 1998

[54] ENHANCED BREAST IMAGING/BIOPSY SYSTEM EMPLOYING TARGETED ULTRASOUND

[75] Inventor: Morgan W. Nields, Englewood, Colo.

[73] Assignee: Fischer Imaging Corporation, Denver, Colo.

[21] Appl. No.: 730,107

[22] Filed: Oct. 15, 1996

[51] Int. Cl.$^6$ .................... A61B 6/02; A61B 8/00
[52] U.S. Cl. .................... 600/407; 600/429; 600/461; 128/915; 128/916
[58] Field of Search .................... 128/653.1, 660.03, 128/660.07, 662.05, 749, 754, 915–916; 364/413.13–413.14, 413.25; 378/37, 98.8, 205–206; 600/407, 425–429, 461

[56] References Cited

U.S. PATENT DOCUMENTS

| | | | |
|---|---|---|---|
| 2,707,662 | 5/1955 | Goldfield et al. | 311/6 |
| 3,165,630 | 1/1965 | Bielat et al. | 250/58 |
| 3,963,933 | 6/1976 | Henkes, Jr. | 250/456 |
| 3,973,126 | 8/1976 | Redington et al. | 250/444 |
| 4,051,380 | 9/1977 | Lasky | 250/451 |
| 4,099,880 | 7/1978 | Kano | 356/164 |
| 4,249,539 | 2/1981 | Vilkomerson et al. | 128/662.05 |
| 4,341,120 | 7/1982 | Anderson | 73/618 |
| 4,346,717 | 8/1982 | Haerten | 128/662.05 |
| 4,485,819 | 12/1984 | Igl | 128/660 |
| 4,567,896 | 2/1986 | Barnea et al. | 128/662.05 X |
| 4,576,175 | 3/1986 | Epstein | 128/662.05 X |
| 4,613,122 | 9/1986 | Manage | 269/322 |
| 4,618,973 | 10/1986 | Lasky | 378/37 |
| 4,625,555 | 12/1986 | Fuji | 73/597 |
| 4,727,565 | 2/1988 | Ericson | 378/205 |
| 4,750,487 | 6/1988 | Zanetti | 128/303 |
| 4,791,934 | 12/1988 | Brunnett | 128/653 |
| 4,869,247 | 9/1989 | Howard, III et al. | 128/303.1 |
| 4,875,478 | 10/1989 | Chen | 128/303 B |
| 4,890,311 | 12/1989 | Saffer | 378/99 |
| 4,930,143 | 5/1990 | Lungren et al. | 378/37 |
| 5,078,142 | 1/1992 | Siczek et al. | 128/653.1 |
| 5,129,911 | 7/1992 | Siczek et al. | 606/130 |
| 5,285,772 | 2/1994 | Rattner | 128/24 EL |
| 5,289,520 | 2/1994 | Pellegrino et al. | 128/662.05 |
| 5,320,111 | 6/1994 | Livingston | 128/754 |
| 5,398,690 | 3/1995 | Batten et al. | 128/662.06 X |
| 5,409,497 | 4/1995 | Siczek et al. | 606/130 |
| 5,411,026 | 5/1995 | Corol | 128/660.03 |
| 5,415,169 | 5/1995 | Siczek et al. | 128/653.1 |
| 5,426,685 | 6/1995 | Pellegrino et al. | 600/429 X |
| 5,447,154 | 9/1995 | Cinquin et al. | 128/653.1 |
| 5,474,072 | 12/1995 | Shmulewitz | 128/660.09 |
| 5,479,927 | 1/1996 | Shmulewitz | 128/660.09 |
| 5,526,394 | 6/1996 | Siczek et al. | 378/37 |
| 5,569,266 | 10/1996 | Siczek | 606/130 |
| 5,584,292 | 12/1996 | Cheung | 128/653.1 |

OTHER PUBLICATIONS

Jan Bolmgraaen, Bertil Jacobson and Bjorn Nordenstrom, "Stereotaxic Instrument for Needle Biopsy of the Mamma" J Roenigenol 129:121–125, Jul. 1977.

Kossoft, G. et al "Apparatus for UTS Examination" Intnl Pub. No. WO 83/02053 Published 23 Jun. 1983.

*Primary Examiner*—Francis Jaworski
*Attorney, Agent, or Firm*—Holme, Roberts & Owen LLP

[57] ABSTRACT

The present invention provides for x-ray imaging and ultrasound imaging of a body region of interest in a spatially correlatable manner. The resultant x-ray and ultrasound images may be combinatively employed to provide three-dimensional information regarding a location of interest within the body, and is particularly apt for use in the analysis/biopsy of potential lesions and suspicious masses in a female breast. The invention provides for direct body contact by an ultrasound imaging head, as well as targeted ultrasound imaging of a selected portion of the region from which x-ray images are obtained.

18 Claims, 6 Drawing Sheets

ENHANCED BREAST IMAGING/BIOPSY SYSTEM EMPLOYING TARGETED ULTRASOUND

FIELD OF THE INVENTION

The present invention relates to medical imaging/biopsy systems, and more particularly, to an enhanced system that employs x-ray imaging and targeted ultrasound imaging in a combinative, spatially correlatable manner that is particularly apt for breast imaging/biopsy procedures.

BACKGROUND OF THE INVENTION

The benefits of early detection and tissue diagnosis of potential lesions and/or suspicious masses within the body is now well established. Indeed, as medical practice and managed care plans continue to evolve, the role of early detection and tissue diagnosis is ever-increasing. With such emphasis, both efficacy and efficiency are at a premium. Specifically, reduction of the time requirements of highly trained medical personnel, patient office visits and medical equipment costs (e.g., via use of multiple-purpose equipment) are primary objectives for procedures utilized in the early detection and tissue diagnosis of potential lesions and otherwise suspicious masses.

Of particular ongoing interest is the area of mammography and breast biopsy. Currently, it is common for patients to receive regular screening mammograms, wherein two x-ray images are generated for each breast in order to identify potential lesions or masses suspicious for malignancy. In the event of equivocal screening mammograms, further x-ray or ultrasound imaging/exams may be performed to obtain additional information. The obtainment of a diagnostic mammogram and/or an ultrasound exam requires another patient office visit and additional medical personnel time. For example, if the presence of a suspicious mass is confirmed, an ultrasound procedure is performed in order to further characterize the mass. Specifically, a free-hand procedure is performed in which a hand-held ultrasound probe is manipulated on the breast while viewing a display to obtain depth-profile information. As can be appreciated, location of a potential lesion/suspicious mass can be difficult, and the ultrasound images obtained are frequently difficult to mentally associate with the x-ray images. As such, the ability to utilize ultrasound technologists as opposed to experienced physician specialists to perform most breast ultrasound procedures is limited.

Should a breast lesion show signs of malignancy pursuant to diagnostic mammography or ultrasound, a breast biopsy is typically performed. Needle localized surgical biopsy means have recently been giving way to stereotactic x-ray biopsy with automated core needles and tissue removal systems. A patient is typically positioned prone (e.g., on a solid table) with the breast immobilized within a predetermined frame of reference (e.g., the breast passes through an opening in the table and is immobilized between opposing compression plates). Stereotactic X-ray images are then generated (e.g., via x-ray film or digital imaging) for review by medical personnel to identify a specific location of interest (e.g., corresponding with a potential lesion or suspicious mass) within the predetermined frame of reference. A puncture instrument, mounted in predetermined relation to the predetermined frame of reference, is then positioned/utilized to obtain a sample of tissue from the location of interest. Of note, current state-of-the-art breast biopsy systems include the MAMMOTEST® and MAMMOVISION® products offered by Fischer Imaging Corporation of Denver, Colo. Such system is further described in U.S. Pat. Nos. 5,078,142, 5,240,011 and 5,415,169, hereby incorporated by reference in their entirety.

While all breast lesions may typically be biopsied utilizing stereotactic x-ray imaging, only recently have technical improvements in ultrasound allowed certain lesions to be biopsied under ultrasound guidance (i.e., with hand-held ultrasound probe and/or biopsy means). In this regard, ultrasound may be preferred due to the lack of ionizing radiation and the availability of real time imaging to reduce procedure time.

Recent developments in tissue removal systems have resulted in larger, heavier devices that are difficult for a physician to use in conjunction with free-hand ultrasound guidance. As an example, the MAMMOTOME® from Biopsys Medical, Inc. of Irvine, Calif. allows rapid removal of breast tissue through a small puncture hole in the breast. Due to the weight and size of the device, physicians are performing more stereotactic x-ray procedures with the MAMMOTOME® due to the solid support of the device by prone stereotactic tables.

In the event that analysis of tissue by histopathologic techniques indicates that a lesion or undesirable mass should be removed from a breast, the surgeon will typically review the various breast images previously obtained to develop a therapeutic surgical strategy, with the goal of removing the entire potential lesion and/or suspicious mass while achieving acceptable cosmetic results.

SUMMARY OF THE INVENTION

It is an object of the present invention to provide an enhanced imaging/biopsy system that can reduce trained medical personnel time requirements in diagnostic and biopsy procedures for tissue diagnosis. It is a related objective to provide such a system in a cost-effective manner; namely through the provision of a system having relatively expensive components that can be utilized for multiple medical procedures combinatively employed in a single system.

A further objective of the present invention is to provide an enhanced imaging/biopsy system for obtaining spatially correlated three-dimensional image information regarding a location of interest in the body, such system being apt for the obtainment of three-dimensional image information regarding a potential lesion or suspicious mass in a female patient's breast. It is a further objective to provide such information in a manner allowing for enhanced use of tissue removal systems used for obtaining tissue samples from the body, including specifically, tissue from a potential lesion or suspicious mass within a female patient's breast.

These and additional objectives are met by the present invention through combinative use of x-ray imaging and targeted ultrasound imaging. More particularly, the present invention provides for the transmission of x-ray radiation through a selected body region-of-interest within a predetermined, three-dimensional frame of reference to obtain x-ray image data corresponding with one or more x-ray images. Additionally, an ultrasound signal is directed into a limited, selectively targeted portion of the x-rayed body region of interest to provide ultrasound image data corresponding with one or more ultrasound images of the targeted portion of the selected body region. The x-ray and ultrasound image data are acquired in spatial co-relation by utilizing x-ray imaging means and ultrasound imaging means each supportably positioned in known co-relation to the predetermined, three-dimensional frame of reference.

This arrangement allows the x-ray and ultrasound image data to combinatively provide correlated, three-dimensional image data corresponding with the body region of interest. In turn, the spatially correlated information allows for an enhanced medical diagnosis of a given location of interest within the body region (e.g., potential lesion or suspicious mass in a breast application) and enhanced biopsy options in relation thereto.

In one aspect of the present invention, the ultrasound imaging means is advantageously positionable in direct contact with the body region of interest for optimal ultrasound image acquisition. More particularly, in breast imaging applications, opposing compression plates may be employed to immobilize a patient's breast within the predetermined, three-dimensional frame of reference, wherein an opening is provided in one of the compression plates for selectively positioning an ultrasound imaging head (e.g., comprising a linear ultrasound transducer array) therethrough in contact with the patient's breast for imaging.

In another aspect of the present invention, a locating means (e.g., an image data processor with display/user interface) is provided for using the x-ray and ultrasound image data to identify a particular location of interest within the body region of interest; and a biopsy means is provided for obtaining a sample from the identified location of interest. In this regard, the biopsy means may include positioning means for selectively and supportably positioning an elongated puncture instrument or other tissue removal system relative to the predetermined, three-dimensional frame of reference, including for example positioning at a desired entry angle.

In a further related aspect of the present invention, the ultrasound imaging means may also comprise a means for selectively positioning an elongated ultrasound imaging head in a known position relative to the predetermined, three-dimensional frame of reference, including angulation of the ultrasound imaging head relative to the predetermined frame of reference. In the latter regard, the imaging head may be angled to image a layer, or "slice," of the body region of interest from a direction orthogonal to a direction from which an angled puncture instrument or other tissue-removal system may be advanced within such layer (i.e., the longitudinal axes of the imaging head and puncture instrument are parallel). Such ultrasound imaging allows for processor simulation/display of a biopsy procedure using a tissue-removal system from a given biopsy position, as well as real-time imaging/control of a biopsy device as it is actually advanced into the body region of interest.

As indicated above, the acquired x-ray images may be employed to select a limited, or targeted, portion of the x-rayed body region of interest to be imaged utilizing the ultrasound signal. Such targeted ultrasound imaging avoids the acquisition, storage and processing of unneeded imaging data, and otherwise facilitates efficient use of medical personnel time, and otherwise advantageously accommodates direct contact with the body portion to be imaged.

Additional features and advantages of the present invention will become apparent upon consideration of the further description provided herein.

DETAILED DESCRIPTION

Figure 1:
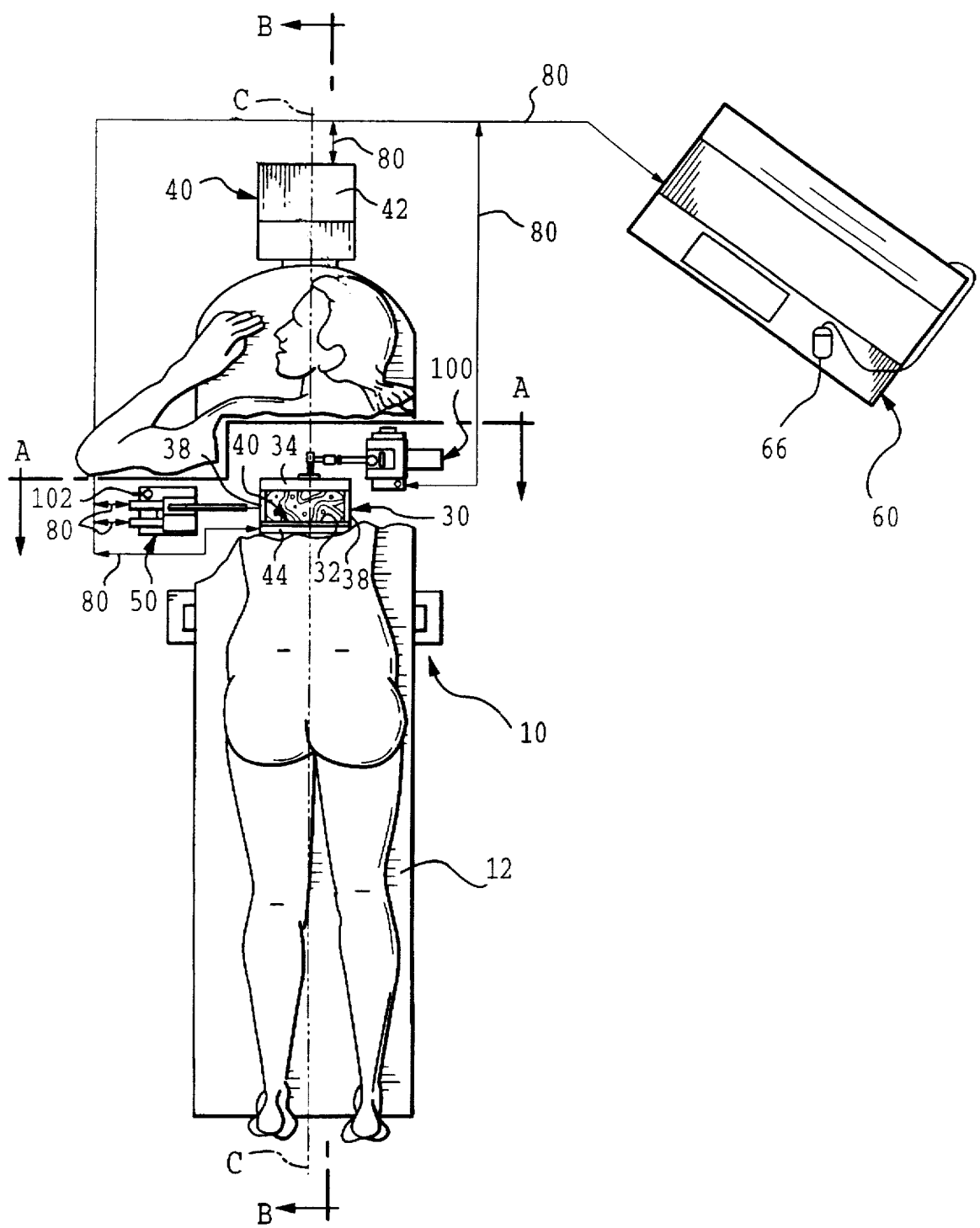
FIG. 1 is a top view of a stereotactic x-ray imaging system with integrated ultrasound imaging and biopsy components combinatively defining one embodiment of the present invention with a central patient/table portion cutaway to show key components.

FIGS. 1–6 illustrate a diagnostic ultrasound/x-ray biopsy system embodiment of the present invention, as adapted for mammography/breast biopsy use.

Generally, the system comprises a support assembly 10 having a patient table 12 with breast-opening 14 therethrough, an immobilization assembly 30 for immobilizing a patient's breast within a predetermined XYZ frame of reference under the opening 14 of table 12, an x-ray imaging assembly 40 for providing two-dimensional x-ray images (e.g., X–Y images) of the patient's immobilized breast in correlated spatial relation to the predetermined XYZ frame of reference, and an ultrasound imaging assembly 100 for providing orthogonal depth-profile images (e.g., X–Z, Y–Z and/or X,Y–Z images) of the immobilized breast in correlated spatial relation to the predetermined XYZ frame of reference. A biopsy assembly 50 having puncture instrument 52 is also provided for obtaining samples from a patient's breast while the breast is immobilized in the predetermined XYZ frame of reference. A display/processor assembly 60 is provided for recording/displaying the various images obtained/generated, for determining the coordinates of a user-identified location of interest within the breast and for monitoring/controlling/simulating the position of the various positionable assembly components.

As will be appreciated, the illustrated embodiment may utilize the x-ray, automated biopsy and other functionalities embodied in the current MAMMOTEST® and MAMMOVISION® products of Fischer Imaging Corp. of Denver, Colo., U.S.A. In this regard, the present invention allows for the integration and effective use of ultrasound imaging with such products, thereby allowing medical equipment cost efficiencies to be realized. As noted previously, the MAMMOTEST® and MAMMOVISION® products include features corresponding with the disclosures in U.S. Pat. Nos. 5,078,142, 5,240,011 and 5,415,169, which are incorporated by reference in their entirety.

Support assembly 10 further includes pedestal 16 and cantilevered first and second support arms 20 and 22, respectively, for supportably interfacing the breast immobilization assembly 30, x-ray imaging assembly 40, ultrasound imaging assembly 100 and biopsy assembly 50 in a predetermined spatially correlated manner. First and second supports arms 20 and 22 can be jointly pivoted relative to pedestal 16, thereby providing imaging/biopsy access to the breast from different directions (e.g., 0°, +90° and −90° relative to the table longitudinal axis). Additionally, second support arm 22 can be selectively pivoted relative to first support arm 20, to provide for stereotactic x-ray imaging (e.g., +15° and −15° relative to the first support arm longitudinal axis).

Breast immobilization assembly 30 is supported on first support arm 20 and includes a stationary face plate 32 and opposing compression paddle 34 for immobilizing a patient's breast therebetween. Compression paddle 34 is x-ray transmittent and further includes a window 36 for direct breast access by the ultrasound imaging assembly 100 and/or biopsy assembly 50. Compression paddle 34 is selectively positionable along first support arm 20 (e.g., via motorized and position sensor systems) for controlled, registered movement toward/away from face plate 32 to accommodate breast positioning/removal and differing breast sizes. Compression paddle 34 can be readily removed from/ interconnected to the first support arm 20 to accommodate the selective use of compression paddles of differing sizes, shapes, window positions, etc. As shown in FIG. 1, compression assembly 30 may further include selectively advanceable/retractable auxiliary side paddles 38, each having optional openings for breast access (e.g., by a puncture instrument or an ultrasound imaging head) for further compression/breast immobilization within the predetermined XYZ frame of reference, and particularly during use of biopsy assembly 50. In this regard, compression paddle 34 and face plate 32 are intended to define a breast imaging area of substantially common thickness and to immobilize such area during imaging/biopsy procedures, and to otherwise provide direct access to the breast for targeted ultrasound imaging/biopsy procedures.

X-ray imaging assembly 40 includes x-ray tube source 42 mounted on the end of second support arm 22 and x-ray receiver/imager 44 mounted on first support arm 20. As will be appreciated, x-ray tube source 42 provides x-ray radiation having a center axis C substantially perpendicular to the fronts of face plate 34 and x-ray receiver/imager 44, such x-ray radiation having a focal point positioned along the center axis C at a determinable location between the face plate 32 and compression paddle 34 during use. In this regard, and by way of example only, the predetermined XYZ frame of reference can be defined in the illustrated embodiment in relation to an X–Y plane corresponding with the front surface of the face plate 32 and/or parallel back surface of compression paddle 34, together with orthogonal X–Z and Y–Z planes within which the x-ray radiation center axis passes (i.e., all three planes being orthogonal). X-ray opaque markings (not shown) can be provided on compression paddle 34 and/or face plate 32 to facilitate spatial correlation of the radiation center axes and x-ray receiver/imager.

In the illustrated embodiment, the x-ray receiver/imager 44 is disposed in abutting relation with the face plate 32. X-ray receiver/imager 44 may comprise an image receptor consisting of a removable radiographic film cassette (e.g., for full-field breast imaging) and/or digital camera (e.g., for partial field, real-time imaging/display). In the latter regard, a partial field, digital CCD camera 46 (e.g., having a 5 mm×10 mm or 5 mm×5 mm imaging area) may be disposed for selective, driven XY movement (e.g., via a servo-drive arrangement) in registered relation to the predetermined XYZ frame of reference.

In the illustrated embodiment, ultrasound imaging assembly 100 and biopsy assembly 50 are selectively and alternatively connectable to opposing sides of first support arm 20 via connection/locking handles 102 and 55, respectively. Additionally, biopsy assembly 50 may be mounted in an axially aligned manner on first support arm 20 for breast access through window 36. A reference, or "home," position for each assembly in a given mounted location is known relative to the predetermine XYZ frame of reference. Further, positioning of the various components of each assembly during use is automatically determinable via position sensor/control systems. As will be appreciated, such positioning can be automated via corresponding processor-controlled, servo motors.

Biopsy assembly 50 comprises a punction sub-assembly 54, which includes puncture instrument 52, and positioner sub-assembly 56. Positioner sub-assembly 56 includes horizontal axis and vertical control motors 58 and 60, respectively, for selective sideward movement and upward angulation of the punction instrument 52. By way of example, punction sub-assembly 56 may comprise the AUTOGUIDE™ assembly of Fischer Imaging Corporation. As will become appreciated, the illustrated embodiment may be particularly apt for use with punction subassemblies for obtaining samples having relatively large cross-sections, including, for example, the MAMMOTOME® from Biopsys Medical, Inc. of Irvine, Calif.

Ultrasound imaging assembly 100 comprises an ultrasound imaging head, or probe, 110 interconnected to arm assembly 130 and, in turn, to XYZ ultrasound positioning assembly 140. As will be further explained, XYZ ultrasound positioning assembly 140 is employed to selectively position ultrasound imaging head 110 through the window 36 of compression paddle 34 to establish direct breast contact for targeted ultrasound imaging in determinable spatial relation to the predetermined XYZ frame of reference.

Figure 5:
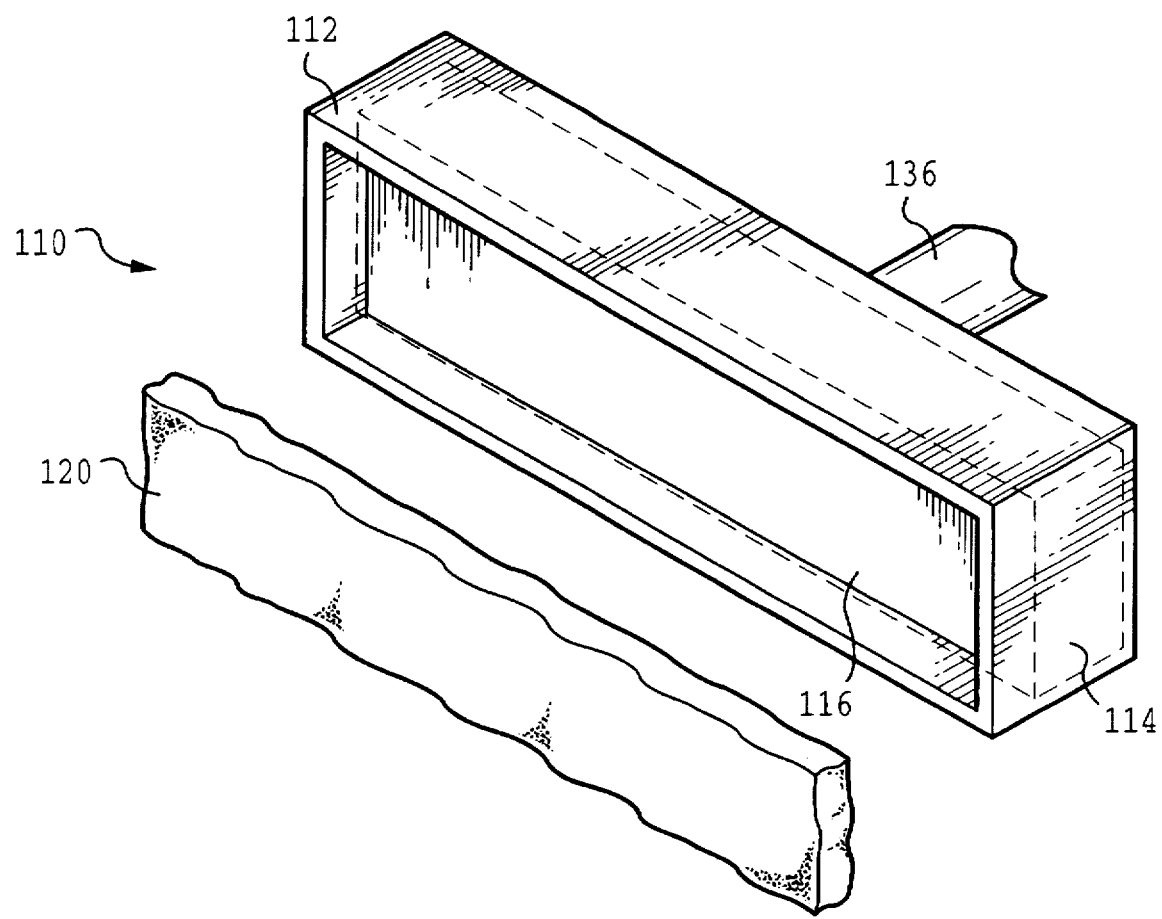
FIG. 5 is a perspective view of an ultrasound imaging head employable in the present invention.

As shown in FIG. 5, ultrasound probe 110 may include an elongated housing 112 with an elongated ultrasound transducer module 114 positioned therein. Ultrasound transducer module 114 provides an ultrasound signal having a focal point on a signal center axis at a location between compression paddle 34 and face plate 32. Ultrasound transducer module 114 may include, for example, a phased linear array of ultrasound transducers positioned along a longitudinal axis of the ultrasound probe 110. The ultrasound probe 110 emits signal pulses and detects corresponding echo pulses to generate the depth-profile images. More particularly, and as will be appreciated by those skilled in the art, detected echo pulses will result from ultrasound transmissivity differences (i.e., ultrasound impedance mismatches) at tissue-type transition areas (e.g., transitions between healthy tissue and a potential lesion/suspicious mass) and at structural obstructions (e.g., the front surface of face plate 32). The housing 112 of ultrasound probe 110 may include a recess 118 (exaggerated in FIG. 5) for receiving a cold-pack 120 for orthogonal application to a biopsy site after a biopsy procedure. Applying pressure and a cold medium directly over a biopsy site in the breast has been shown to reduce hematoma bleeding and bruising.

XYZ ultrasound positioning assembly 140 includes X, Y and Z platforms 142, 146 and 148, respectively, mounted for selective, registered movement on corresponding support members 152, 156 and 158 relative to the predetermined XYZ frame of reference. In this regard, XYZ positioning assembly 140 may include internal X, Y and Z optical position encoders. XYZ positioning assembly 140 can further include X, Y and Z motor drives for automatic, selective positioning of ultrasound imaging head 110 in registered XYZ relation to the predetermined XYZ frame of reference. The XYZ positioning assembly 140 may also include counterbalance and electro-lock components to accommodate ready manual positioning and to maintain a selected ultrasound imaging/biopsy position, respectively.

Arm assembly 130 is provided to allow the ultrasound imaging probe 110 to be rotated about one or more of selected X, Y and Z axes to obtain a desired pitch, roll and/or yaw orientation). For example, arm assembly 130 can be controlled to selectively rotate the longitudinal axis, or pitch, of probe 110 so that the ultrasound signal may be employed to obtain depth-profile image in a plane, or "slice," within which an upwardly angled punction instrument 52 of biopsy assembly 50 may be orthogonally advanced, as will be further discussed.

In the illustrated embodiment, arm assembly 130 includes pivot arm 132 pivotally interconnected to XYZ ultrasound positioning assembly 140 via a lock/release mechanism (not shown) for selective, centered rotation of probe 116 about axis YY. Arm assembly 130 further includes arm 134 rotably interconnected to arm 132 via a lock/release mechanism (not shown) for selective, centered rotation of probe 116 about axis XX, and arm 136 rotably interconnected to arm 134 via a lock/release mechanism (not shown) for selective, centered rotation of probe 116 about axis ZZ. Internal optical encoders (not shown) may be provided at the various arm interconnections, wherein the pitch, roll and/or yaw of probe 110 is automatically determinable in relation to the predetermined XYZ frame of reference. In this regard, internal automated micro-positioners may also be utilized under processor control.

As will be appreciated, the ultrasound signal may be scanned to obtain depth-profile information for a predetermined layer, or "slice," within the region of interest. By way of primary example, such scanning may be provided electrically by driving a phased linear array of transducers comprising probe 110 in a known manner and/or via manual or automatic-driven control of XYZ positioning assembly 140 to mechanically move ultrasound imaging head 110.

Figure 6:
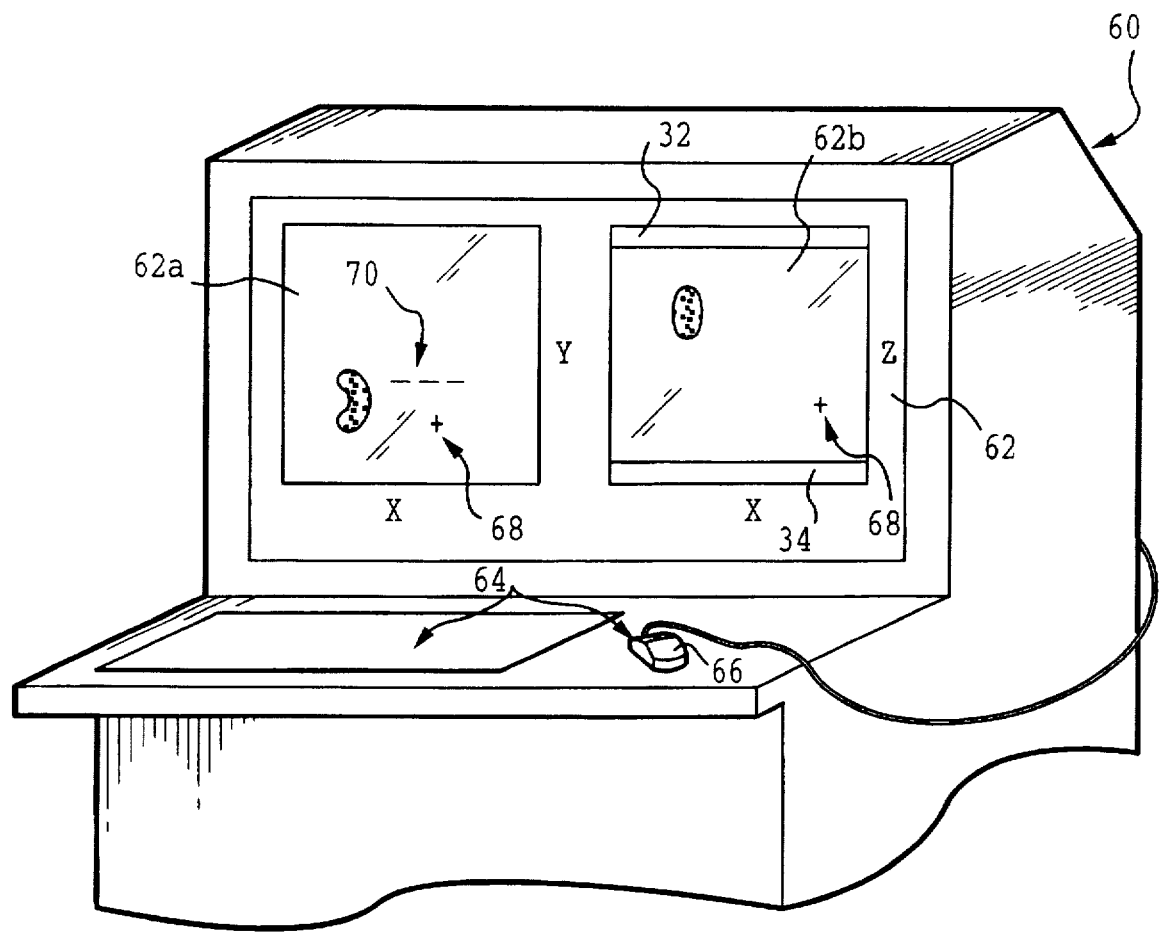
FIG. 6 illustrates spatially correlated x-ray and ultrasound images of a potential breast lesion/suspicious mass obtainable with the present invention.

As shown in FIG. 6, display/processor 60 includes a display screen 62 for displaying the acquired x-ray images on a first portion 62a and displaying corresponding depth-profile ultrasound images on a second portion 62b, each in registered co-relation to the predetermined XYZ frame of reference. Display/processor 60 may further include a user interface means 64, e.g., keyboard 65 and mouse 66 and screen point cursor 68 (e.g., on both display portions 62a, 62b), wherein a user may identify (e.g., click upon) a specific location-of-interest within both an x-ray image and corresponding ultrasound image (e.g., corresponding with a potential lesion or suspicious mass), e.g. for automatic processor determination of the three-dimensional coordinates of the location within the predetermined XYZ frame of reference. User interface means may further allow for user selection/display of a particular desired ultrasound depth-profile image, e.g., via mouse 66 and screen "slice" cursor 70 on the x-ray image display portion 62a. More particularly, screen "slice" cursor 70 may be employed to identify a particular slice, or layer, of an X-Y x-ray image for which a corresponding ultrasound depth-profile image is to be obtained (e.g., thereby resulting in processor-assisted positioning and imaging using probe 110) and/or accessed and displayed (e.g., where such ultrasound depth-profile image has been previously obtained/stored for selective subsequent review).

As indicated, display/processor 60 may be operatively interconnected (e.g., via electrical lines 80) to the various positionable assembly components for monitoring/controlling their respective positions relative to the predetermined XYZ frame of reference, including the positionable components of immobilization assembly 30, x-ray imaging assembly 40, ultrasound imaging assembly 110 and biopsy assembly 50. By way of primary example, display/processor 60 may determine the three-dimensional coordinates of a specific location of interest, as described above, and in turn assist/control the positioning of biopsy assembly 50 so as to position the assembly for obtainment of a tissue sample from the location of interest. In this regard, the display/processor 60 may also be employable to visually project, or simulate, the entry of a punction instrument 52 into a given location of interest, thereby allowing physicians the opportunity to insure an optimal positioning for biopsy entry prior to an actual biopsy procedure. Since three-dimensional visualization of a potential lesion/suspicious mass can be provided by the present invention, and since the disclosed arrangement allows for breast access by biopsy assembly 50 from a plurality of aspects (e.g., by selective mounting on either side of or coaxial along support arm 20), such simulated biopsy modeling may prone to be of particular advantage.

The present invention allows for spatial correlation of the x-ray and ultrasound images utilizing various techniques. By way of primary example, it can be appreciated that the X-Y x-ray images obtained can be readily correlated to the predetermined XYZ frame of reference since the position and attributes of x-ray source 42 and x-ray receiver/imager 44 are each known in relation to the predetermined XYZ frame of reference. Additionally, in stereotactic imaging procedures, the two X-Y stereotactic x-ray images can be employed to obtain a Z location for particular location of interest relative to the predetermined XYZ frame of reference utilizing known triangulation techniques, as will be appreciated by those skilled in the art. Further, the XYZ positioning of ultrasound imaging head 110 is determinable relative to the predetermined XYZ frame of reference, as noted above. Relatedly, in the embodiment described above, the ultrasound imaging head 110 will emit/detect ultrasound signals in substantially the same plane as the surface of compression paddle 34 contacting the imaged breast. The position of such surface relative to the predetermined XYZ frame of reference (e.g., the Z distance to face plate 32) is also determinable. In view of the foregoing, it can be seen that utilizing known ultrasound pulse/echo techniques a depth profile comprising a potential lesion/suspicious mass can be spatially related in a reliable manner to the acquired x-ray images.

In use, a patient can be positioned on the table 12 with a breast positioned through opening 14. Compression paddle 34 is then advanced along first support arm 20 to compress the breast to define a cross-sectional imaging area having a common thickness and to otherwise immobilize the breast in a set position within the predetermined XYZ frame of reference. X-ray imaging assembly 40 is then selectively positioned to obtain the desired x-ray images. Such x-ray images are then reviewed using display/processor 60, to identify, analyze and or otherwise confirm the presence and location of a potential lesion or suspicious mass for ultrasound imaging. Alternatively, the general location of a potential lesion or suspicious mass may already be known due to prior x-ray screening.

In either case, to proceed with ultrasound imaging, the patient should be positioned/repositioned so that the potential lesion or suspicious mass is positioned within the accessible field of view of ultrasound imaging head 110 when it is maneuvered through the window 36 of compression paddle 34 in direct contact with the imaged breast. As can be appreciated, in order for the present invention to yield spatially correlatable image information with respect to a potential lesion or suspicious mass, new x-ray and corresponding ultrasound images should be generated for each position in which a breast is immobilized within the predetermined XYZ frame of reference. As such, the benefit of utilizing a digital camera 46 in x-ray receiver 44 for partial field, real-time imaging via display/processor 60 can be readily understood.

Once it is verified that the area of interest is positioned adjacent to the window 36, ultrasound imaging probe 110 is positioned through the window 36 and a series of ultrasound images are obtained and displayed on display/processor 60. Cursor 66 control of the ultrasound images taken across the area of interest provides additional, valuable information as to the type of potential lesion/suspicious mass originally noted on an original mammogram. For example, with proper training of ultrasound and x-ray imaging techniques, physicians may rule out the possibility of a solid mass in favor of a fluid-filled cyst. Or, additional ultrasound characteristics may aid the physician in making a definitive diagnosis.

If it is determined that a biopsy is desired, the specific location from which tissue is to be obtained can be identified using mouse 66 to position screen point cursor 68 on both the x-ray image and correlated ultrasound depth-profile image on display/processor 60. Three-dimensional coordinates can then be determined and utilized by display/processor 60 to control positioning of biopsy assembly 50. In this regard, it will be appreciated that specific attributes of the particular punction subassembly 54 utilized will have been previously entered into by display/processor 60. Further, and as noted above, given such previous input information, display/processor 60 may be employed to simulate the advancement of punction instrument 52 into the breast from a given potential position, thereby allowing the physician to determine if breast biopsy access from a different position may be more desirable.

Figure 2:
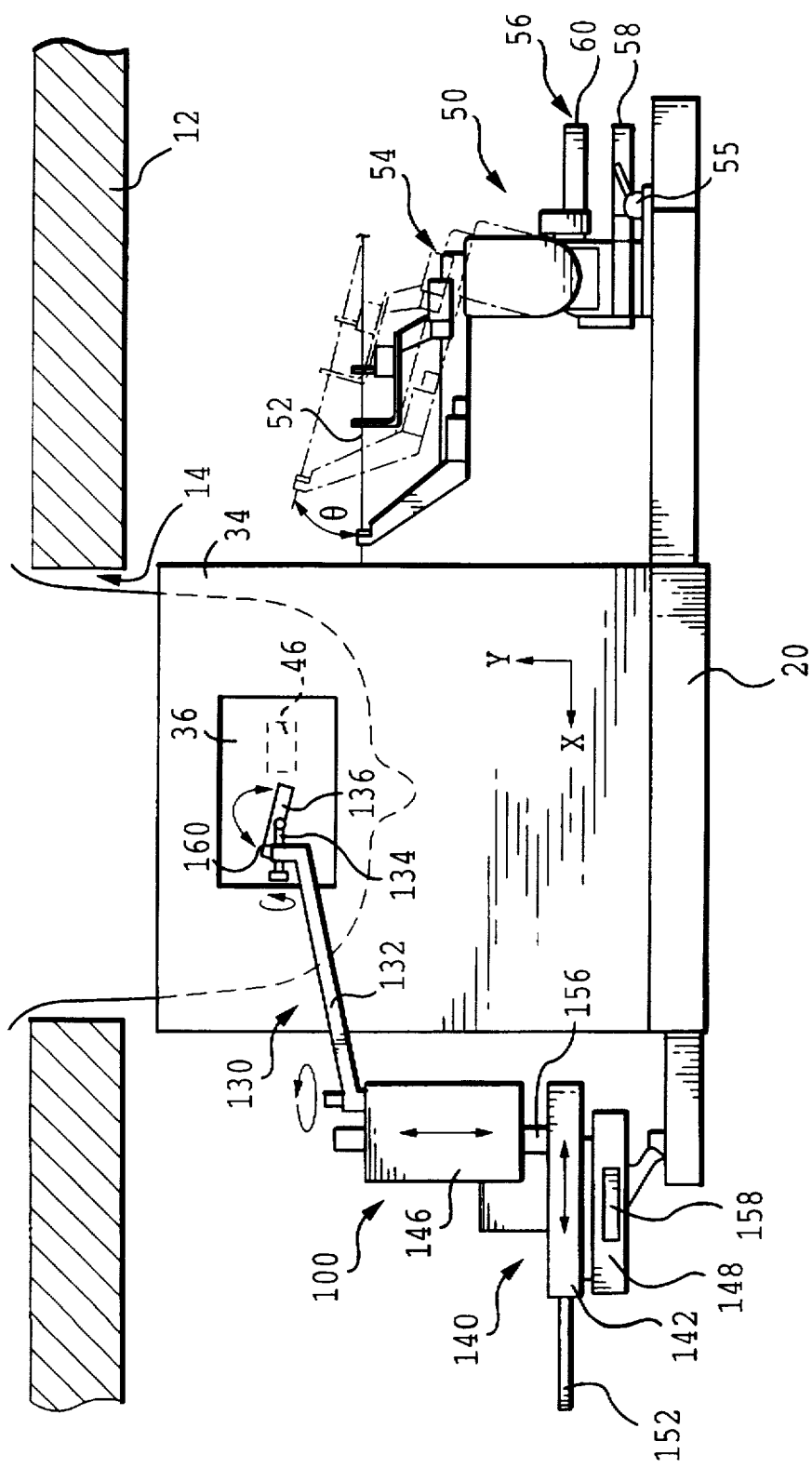
FIG. 2 is a partial end cross-sectional view of the embodiment of FIG. 1 cut along AA.
Figure 3:
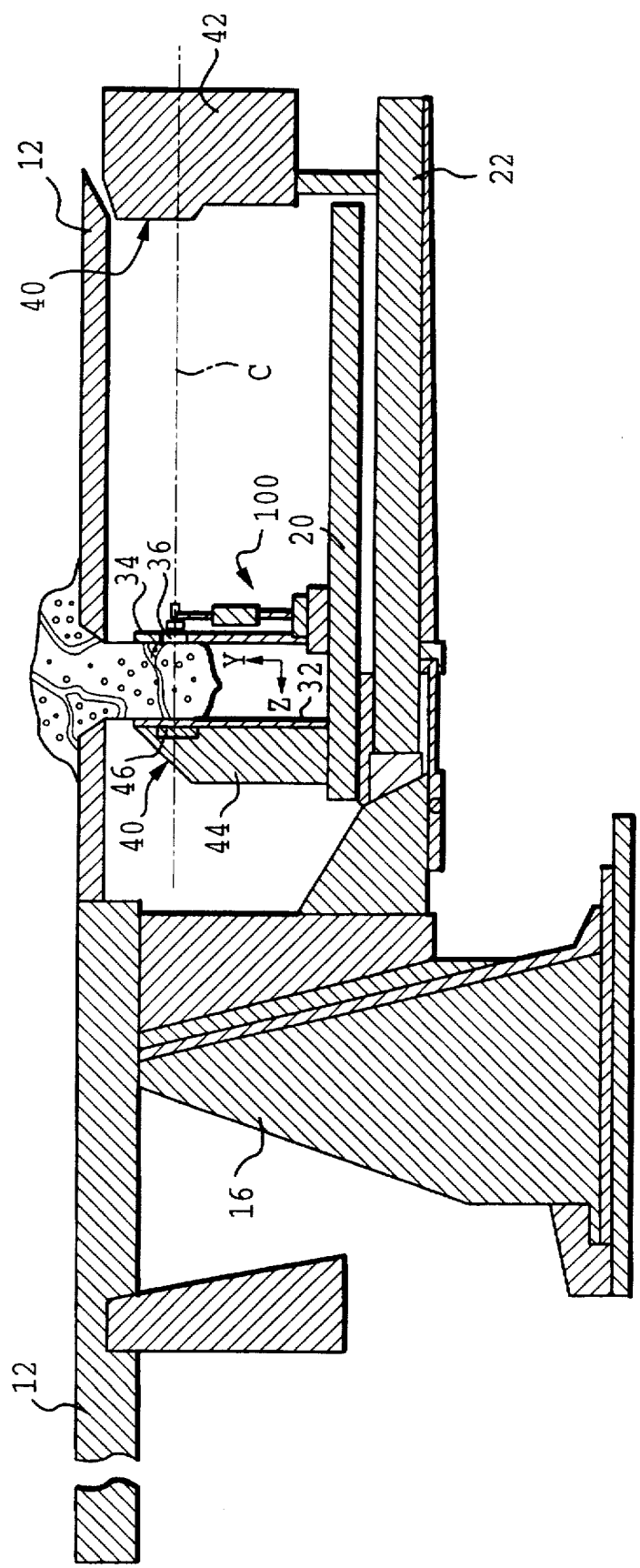
FIG. 3 is a partial side cross-sectional view of the embodiment of FIG. 1 cut along BB.
Figure 4:
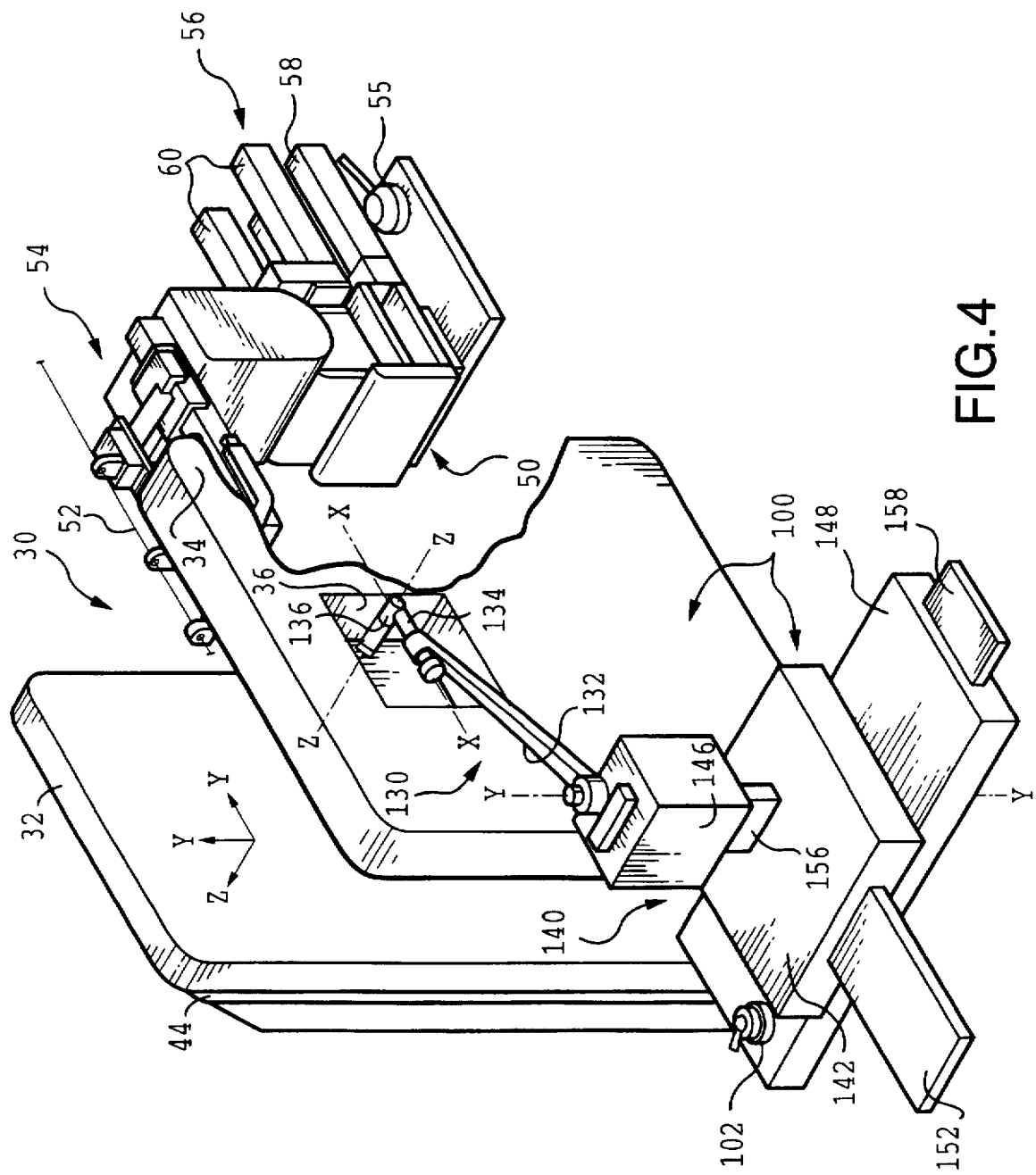
FIG. 4 is a perspective view of the immobilization, ultrasound imaging and biopsy assemblies of the embodiment of FIG. 1.

After the biopsy subassembly 50 is positioned as desired, biopsy procedures may be completed. In conjunction with such procedures, the ultrasound imaging head 110 may be utilized to provide continuous, successive depth profile images, thereby allowing for real-time monitoring and user control of the advancement of the punction instrument 52 into the breast. More particularly, when the punction instrument is positioned at an angle θ as illustrated in FIG. 2, ultrasound imaging head 110 may be similarly angled at θ (e.g., relative to horizontal) so as to yield real-time ultrasound depth-profile images of the layer into which punction instrument 52 is advanced. After biopsy procedures are completed, ultrasound imaging head 110 may be repositioned so as to allow for pressure application of a cold pack 120.

While the present invention has been described in relation to one embodiment, it will be appreciated that the invention may be utilized in numerous additional embodiments and procedures. Such additional embodiments and procedures are within the scope of the present invention, as defined by the claims which follow.

What is claimed:

1. A medical apparatus, comprising:

x-ray imaging means for transmitting x-ray radiation through a body region of interest positioned within a predetermined, three-dimensional frame of reference, and for providing two-dimensional x-ray image data corresponding with each of one or more x-ray images of the body region of interest;

ultrasound imaging means, positionable in direct contact with said body region of interest, for directing an ultrasound signal into said body region of interest positioned within said predetermined, three-dimensional frame of reference, and for providing ultrasound image data corresponding with one or more ultrasound images of the body region of interest in spatial co-relation to said x-ray images, said ultrasound image data including third-dimensional information regarding the body region of interest, wherein said two-dimensional x-ray image data and said ultrasound image data including said third-dimensional information combinatively provide correlated, three-dimensional image data corresponding with the body region of interest.

2. A medical apparatus, as recited in claim 1, further comprising:

means for using said x-ray and ultrasound image data to identify a location of interest within said body region of interest; and biopsy means, positionable in predetermined relation relative to said predetermined, three-dimensional frame of reference, for obtaining a sample from said location of interest.

3. A medical apparatus, as recited in claim 2, wherein:

said biopsy means includes:

a puncture instrument; and positioning means for selectively positioning said puncture instrument at an entry angle relative to said predetermined, three-dimensional frame of reference; and said ultrasound imaging means comprises:

an ultrasound imaging probe; and means for selectively positioning said imaging probe relative to said predetermined, three-dimensional frame of reference, wherein the longitudinal axis of the ultrasound probe is aligned with the entry angle of the puncture instrument such that the puncture instrument is imaged in real time as it is entered into the breast.

4. A medical apparatus as recited in claim 1, wherein said body region of interest is a female breast, and the apparatus further comprises:

an immobilization means for immobilizing said breast between first and second compression members, said first compression member having an opening therethrough, wherein said ultrasound imaging means is selectively positionable through said opening to directly contact the breast.

5. A medical apparatus as recited in claim 4, said x-ray imaging means comprising:

an x-ray source for providing said x-ray radiation; and an x-ray receiver for receiving x-ray radiation passing through said breast, said x-ray receiver being positionable immediately adjacent to said second compression member.

6. A medical apparatus as recited in claim 5, said x-ray receiver comprising:

a digital camera selectively moveable and positionable within a plane substantially to perpendicular to a center axis of said x-ray radiation; and user display and interface means for user identification, using an acquired and displayed x-ray image, of an acquired ultrasound image to be displayed.

7. A medical apparatus as recited in claim 1, comprising:

display means for displaying said x-ray and ultrasound images in registered correlation.

8. A method for use in performing a medical procedure, comprising:

positioning a body region of interest within a predetermined frame of reference;

x-ray imaging said body region of interest with x-ray radiation to obtain two-dimensional x-ray image data corresponding with each of one or more x-ray images;

using said one or more x-ray images to identify a location of interest within a selected, limited portion of said body region of interest, said selected limited portion being smaller than said imaged body region; and ultrasound imaging only said selected, limited portion of said body region of interest with an ultrasound signal to obtain targeted ultrasound image data corresponding with one or more ultrasound images, said ultrasound image data including third-dimensional information regarding the body region of interest, wherein said two-dimensional x-ray image data and said ultrasound image data including said third-dimensional information combinatively provide correlated three-dimensional image data corresponding with the selected, limited portion.

9. The method as recited in claim 8, said ultrasound imaging step comprising:

contacting said selected, limited portion of said body region of interest with an ultrasound imaging means.

10. The method as recited in claim 9, said ultrasound imaging step further comprising:

scanning said ultrasound signal across said selected, limited portion of said body region of interest.

11. The method as recited in claim 8, said using step comprising:

displaying said one or more x-ray images for visual review.

12. The method as recited in claim 8, further comprising:

employing said x-ray image data and ultrasound image data to position a punction instrument for obtainment of a sample from said location of interest.

13. The method as recited in claim 12, said employing step comprising:

using said ultrasound image data while inserting said punction instrument into said breast.

14. The method as recited in claim 8, further comprising:

generating a three-dimensional model of said location of interest utilizing said x-ray image data and ultrasound image data.

15. A method for use in performing a medical procedure, comprising:

positioning a body region of interest within a predetermined frame of reference;

supportably mounting a biopsy device in known spatial relation relating to and on a first side of said predetermined frame of reference;

ultrasound imaging at least a portion of said body region of interest to obtain ultrasound image data by supportably mounting an ultrasound imaging probe in known spatial relation to and on a second side of said predetermined frame of reference, the second side being adjacent to said first side and contacting said ultrasound imaging probe with said body region of interest;

x-ray imaging said body region of interest from said second side of said predetermined frame of reference by supportably mounting an x-ray imaging source and an x-ray image receiver in known spatial relation to and on opposing sides of said predetermined frame of reference;

employing said ultrasound image data to selectively position said biopsy device relative to said predetermined frame of reference, and obtaining a sample from said portion of said body region of interest with said biopsy device.

16. The method as recited in claim 15, wherein: said ultrasound imaging step comprises:

displaying in real-time ultrasound images of said portion of said body region of interest; and said obtaining step comprises:

advancing said biopsy device into said body region of interest while contemporaneously viewing said real-time ultrasound images.

17. The method as recited in claim 15, further comprising:

immobilizing said body region of interest between first and second plates defining said opposing sides of said predetermined frame of reference.

18. The method as recited in claim 17, said ultrasound imaging step further comprising:

positioning said ultrasound imaging probe through said first plate and in direct contact with said body region of interest.

* * * * *